US008105611B2

(12) United States Patent
Tong et al.

(10) Patent No.: US 8,105,611 B2
(45) Date of Patent: Jan. 31, 2012

(54) TREATMENT OF AUTOIMMUNE DISORDER WITH A NEUROTOXIN

(75) Inventors: Kenneth L. Tong, Carlsbad, CA (US); Pamela D. Van Schaack, Costa Mesa, CA (US)

(73) Assignee: Allergan, Inc., Irvine, CA (US)

( * ) Notice: Subject to any disclaimer, the term of this patent is extended or adjusted under 35 U.S.C. 154(b) by 561 days.

(21) Appl. No.: 11/156,502

(22) Filed: Jun. 17, 2005

(65) Prior Publication Data

US 2006/0286127 A1 Dec. 21, 2006

(51) Int. Cl.
*A61K 39/02* (2006.01)
*A61K 39/08* (2006.01)

(52) U.S. Cl. ............... 424/236.1; 424/239.1; 424/247.1

(58) Field of Classification Search .............. 424/184.1, 424/234.1, 236.1, 247.1, 423, 424; 530/300
See application file for complete search history.

(56) References Cited

U.S. PATENT DOCUMENTS

| | | | |
|---|---|---|---|
| 5,437,291 A | 8/1995 | Pasricha et al. | |
| 5,670,484 A | 9/1997 | Binder | |
| 5,714,468 A | 2/1998 | Binder | |
| 5,766,605 A | 6/1998 | Sanders et al. | |
| 5,989,545 A | 11/1999 | Foster et al. | |
| 6,063,768 A * | 5/2000 | First ...................... | 514/14 |
| 6,139,845 A | 10/2000 | Donovan | |
| 6,143,306 A | 11/2000 | Donovan | |
| 6,261,572 B1 | 7/2001 | Donovan | |
| 6,265,379 B1 | 7/2001 | Donovan | |
| 6,299,893 B1 | 10/2001 | Schwartz et al. | |
| 6,306,423 B1 | 10/2001 | Donovan et al. | |
| 6,306,432 B1 * | 10/2001 | Shirley et al. ................. | 424/450 |
| 6,312,708 B1 | 11/2001 | Donovan | |
| 6,337,075 B1 | 1/2002 | Donovan | |
| 6,358,917 B1 * | 3/2002 | Carruthers et al. ............... | 514/2 |
| 6,358,926 B2 | 3/2002 | Donovan | |
| 6,383,509 B1 * | 5/2002 | Donovan et al. ............. | 424/423 |
| 6,416,765 B1 | 7/2002 | Donovan | |
| 6,423,319 B1 | 7/2002 | Brooks et al. | |
| 6,458,365 B1 | 10/2002 | Aoki et al. | |
| 6,464,986 B1 | 10/2002 | Aoki et al. | |
| 6,506,399 B2 | 1/2003 | Donovan | |
| 6,585,993 B2 | 7/2003 | Donovan et al. | |
| 6,632,440 B1 | 10/2003 | Quinn et al. | |
| 6,787,517 B1 * | 9/2004 | Gil et al. .......................... | 514/1 |
| 7,022,329 B2 * | 4/2006 | Donovan ................... | 424/239.1 |
| 2002/0102274 A1 | 8/2002 | Voet et al. | |

FOREIGN PATENT DOCUMENTS

WO   WO 2005/051291   9/2005

OTHER PUBLICATIONS

Weyand et al (Curr. Opin. Rheumatol., vol. 11(3), May 1999).*
Choy (New England Journal of Medicine, vol. 344, No. 12, Mar. 22, 2001), 907-916.*
Moulian et al (Annals of the New York Academy of Sciences 841:397-406, 1998).*
Wang et al (Am. J. Roentgenol., 181, No. 3, 721-24, 2003)(Abstract only).*
Shiono et al (International Immunology, Aug. 2003, vol. 15, No. 8, p. 903-912) (Abstract only).*
Widmer et al (Current Opinion in Biotechnology, 1991, 2:872-876).*
Moguel-Ancheita et al (Archivos de la Sociedad Espanola de Oftalmologia, Jan. 2003, vol. 78, No. 1, pp. 9-14)(Abstract only)).*
Ueno et al (Clinical Exp. Immunol., 1980, 42, 463-469).*
Verheyden et al (Dis Mon 2002; 48:357-366).*
U.S. Appl. No. 10/194,805.
Aoki K., et al, "Mechanisms of the antinociceptive effect of subcutaneous Botox: Inhibition of peripheral and central nociceptive processing", *Cephalalgia* Sep. 2003;23(7):649.
Bigalke H., et al., "*Botulinum* A Neurotoxin Inhibits Non-Cholinergic Synaptic Transmission in Mouse Spinal Cord Neurons in Culture", *Brain Research* 360;318-324:1985.
Bigalke H., et al., "Tetanus Toxin and Botulinum A Toxin Inhibit Release and Uptake of Various Transmitters, as Studied with Particulate Preparations From Rat Brain and Spinal Cord", *Naunyn-Schmiedeberg's Arch Pharmacol* 316;244-251:1981.
Binz T. et al., "The Complete Sequence of Botulinum Neurotoxin Type A and Comparison with Other Clostridial Neurotoxins", *J Biological Chemistry* 265(16);9153-9158:1990.
Bushara K., "Botulinum toxin and rhinorrhea", *Otolatyngol Head Neck Surg* 1996;114(3):507.
Choy et al., "Cytokine Pathways and Joint Inflammation in Rheumatoid Arthritis", *N. Engl. J. Med*, vol. 344, No. 12, pp. 907-916, Mar. 22, 2001.
Habermann E., et al., "Tetanus Toxin and *Botulinum* A and C Neurotoxins Inhibit Noradrenaline Release From Cultured Mouse Brain", *J Neurochem* 51(2);522-527:1988.
Habermann, "I-Labeled Neurotoxin from Clostridium Botulinum A: Preparation, Binding to Synaptoxomes and Ascent to the Spinal Cord", *Nauny-Schmiedeberg's Arch. Pharmacol*. 1974; 281, 47-56.
Habermann E., "Inhibition by Tetanus and Botulinum A Toxin of the release of [3H]Noradrenaline and [3H]GABA From Rat Brain Homogenate", *Experientia* 44;224-226:1988. Herold et al., "Anti-CD3 Monoclonal Antibody in New-Onset Type 1 Diabetes Mellitus", *N. Engl. J. Med*., vol. 346, No. 22, pp. 1692-1698, May 30, 2002.
Huang et al., "Truncated SNAP-25(1-197), Like Botulinum Neurotoxin A, Can Inhibit Insulin Secretion from HIT-T15 Insulinoma Cells", *Mol. Endocrinol*. 12(7):1060-70, 1998.
Jankovic J. et al., *Therapy With Botulinum Toxin*, Marcel Dekker, Inc., (1994), p. 5.
Katsambas A., et al., "Cutaneous diseases of the foot: Unapproved treatments", *Clin Dermatol* Nov.-Dec. 2002;20(6):689-699.
Li Y, et al., "Sensory and motor denervation influences epidermal thickness in rat foot glabrous skin", *Exp Neurol* 1997;147:452-462 (see p. 459).
Mackay et al., "Advances in Immunology", *N. Engl J Med*, 345(5):340-350, 2001.
Moyer E et al., *Botulinum Toxin Type B: Experimental and Clinical Experience*, being chapter 6, pp. 71-85 of "Therapy With Botulinum Toxin", edited by Jankovic, J. et al. (1994), Marcel Dekker, Inc.
Pearce, L.B., "Pharmacologic Characterization of Botulinum Toxin for Basic Science and Medicine", *Toxicon* 35(9);1373-1412 at 1393.
Sanchez-Prieto, J., et al., "Botulinum Toxin A Blocks Glutamate Exocytosis From Guinea Pig Cerebral Cortical Synaptosomes", *Eur J. Biochem* 165;675-681:1897.
Shantz, E.J., et al, "Properties and use of Botulinum toxin and Other Microbial Neurotoxins in Medicine", *Microbiol Rev*. 56;80-99:1992.
Singh, *Critical Aspects of Bacterial Protein Toxins*, pp. 63-84 (chapter 4) of Natural Toxins II, edited by B.R. Singh et al., Plenum Press, New York (1976).

(Continued)

Primary Examiner — Vanessa L. Ford
(74) Attorney, Agent, or Firm — Hal Gibson; Debra Condino

(57) ABSTRACT

Methods of treating one or more autoimmune disorders include a step of administering a Clostridial neurotoxin, such as a botulinum toxin, to a patient that has an autoimmune disorder. In one aspect, a method includes a step of administering the neurotoxin to the thymus gland or near the thymus gland of the patient. In another aspect, a method includes a step of administering the neurotoxin in combination with administering a cytokine inhibitor to the patient. Compositions are also described.

27 Claims, No Drawings

OTHER PUBLICATIONS

Sevim, S., et al., "Botulinum toxin-A therapy for palmar and plantar hyperhidrosis", *Acta Neurol Belg* Dec. 2002;102(4):167-70.

Suputtitada, A., "Local botulinum toxin type A injections in the treatment of spastic toes", *Am J Phys Med Rehabil* Oct. 2002;81(10):770-5.

Weigand et al, I-Labelled Botulinum A Neurotoxin: Pharmacokinetics in Cats after Intramuscular Injection, *Nauny-Schmiedeberg's Arch. Pharmacol.* 1976; 292, 161-165.

Balkwill F., "Cytokine amplification and inhibition of immune and inflammatory responses", *J Viral Hepat.* 1997; 4 Suppl 2:6-15.

Begley CG. et al., "Resolving conflicting signals: cross inhibition of cytokine signaling pathways", *Blood.* Mar. 1, 1999;93(5): 1443-7.

Boyd et al., "The insulin secreting β-cell line, HIT-15, contains SNAP-25 which is a target for botulinum neurotoxin-A", *Mov Disord*, 10(3):376:May 1995.

Columbo M.P. et al., "Cytokine gene transfer in tumor inhibition and tumor therapy: where are we now?" *Immunol Today.* Feb. 1994; 15(2):48-51.

Cui M.L. et al., "Subcutaneous Botox® Inhibits Formalin-Induced Local Neurotransmitter Release and Spinal Nociceptive Processing," $10^{th}$ World Congress on Pain, IASP 2002; Poster #834-P104.

Cui M.L. et al., "Botulinum Toxin A Inhibits the Inflammatory Pain in the Rat Formalin Model", *Soc Neurosci* 2000;26 (1-2) Abstract #2462.

Fox D.A., Cytokine blockade as a new strategy to treat rheumatoid arthritis: inhibition of tumor necrosis factor. *Arch Intern Med.* Feb. 28, 2000; 160(4): 437-44.

Gonelle-Gispert et al., "SNAP-25a and -25b isoforms are both expressed in insulin-secreting cells and can function in insulin secretion", *Biochem J* 1;339 (pt 1):159-65:1999.

Gray E. et al. "Inhibition of tissue factor and cytokine release." *Haemostasis.* 1996; 26 Suppl 1: 92-5.

Higgs OA., "Novel approaches to the inhibition of cytokine responses in asthama", J *Pharm Pharmacol.* May 1997; 49 Suppl 3:25-31.

Ishikawa H. et al., "Presynaptic Effects of Botulinum Toxin Type A on the Neuronally Evoked Response of Albino and Pitmented Rabbit Iris Sphincter and Dilator Muscles", *Jpn J Ophthalmol* 2000;44(2):106-109.

Jacks, L., et al., "Idiopathic toe walking: Treatment with botulinum toxin A injection", *Dev Med Child Neurol* 2002;44(Suppl 91):6.

Matsushima K., "Involvement of leukotactic activated cytokine family, chemokines, in human diseases and their inhibition", *Nihon Rinsho Meneki Gakkai Kaishi.* Dec. 1996; 19(6):552-4.

Naumann et al., "Botulinum toxin type A in the treatment of focal, axillary and palmar hyperhydrosis and other hyperhidrotic conditions", *European J. Neurology* 6 (Supp 4): S111-S115:1999.

Nishimoto N. et al., "New therapeutic strategy for autoimmune diseases. 3) Treatment of autoimmune diseases by cytokine signal transduction inhibition". *Nippon Naika Gakkai Zasshi.* Sep. 10, 1998;87(9): 1745-50.

Ragona et al., "Management of Parotid Sialocele With Botulinum Toxin", *The Laryngoscope* 109:1344-1346:1999.

Rogers J., et al., "Injections of botulinum toxin A in foot dystonia", *Neurology* Apr. 1993;43(4 Suppl 2).

Sloop et al., "Reconstituted botulinum toxin type A does not lose potency in humans if it is refrozen or refrigerated for 2 weeks before use", *Neurology*, 48:249-53:Jan. 1997.

Schwiebert L.M. et al., "Glucocorticosteroid inhibition of cytokine production: relevance to antiallergic actions." *J Allergy Clin Immunol.* Jan. 1996; 97(1 Pt 2): 143-52. Review. Erratum in: *J Allergy Clin Immunol* Sep. 1996;98(3):718. Schwiebert LA [corrected to Schwiebert LM].

Strassmann G., et al., "Inhibition of experimental cancer cachexia by anti-cytokine and anti-cytokine-receptor therapy." *Cytokenes Mol Ther.* Jun. 1995;1(2):107-13.

Widmer M.B., Inhibition of cytokine function: potential in autoimmune disease. *Curr Opin Biotechnol.* Dec. 1991;2(6):872-6.

Xolair package insert. 2003 Genentech. www.gene.com.

* cited by examiner

TREATMENT OF AUTOIMMUNE DISORDER WITH A NEUROTOXIN

BACKGROUND

The present invention relates to treatment of autoimmune disorders using a neurotoxin, and more particularly to methods and compositions for treating autoimmune disorders using a Clostridial neurotoxin.

Immune System

The immune system is the body's first line of defense involving a complex of organs, glands, highly specialized cells, and a circulatory system working together to clear infection from the body. The immune system includes two major parts. One part may be referred to as the humoral immune system and is involved in the production of antibodies. The second part may be referred to as the cellular immune system and is the component that includes thymic lymphocytes (T lymphocytes or T cells).

Activated T cells are formed from white blood cells passing through the thymus gland located in the chest of a human patient. The thymus consists of two lobes connected by areolar tissue. The lobes are enclosed in a fibrous capsule which divides the lobes into lobules that consist of an irregular branching framework of epithelial cells and lymphocytes. The thymus contains three major cell populations: (1) epithelial cells, (2) hemopoietic cells, and (3) accessory cells.

Epithelial cells seem to be mainly responsible for the creation of the necessary microenvironments and their factors. Epithelial cells promote different steps of intrathymic T-cell differentiation and maturation. There appears to be at least six different types of epithelial cells: type 1—subcapsular-perivascular cells; type 2—pale epithelial cells, which predominate in the outer cortex; type 3—thymic nurse cells that have the unique feature of emperipolesis; type 4—dark cells that are typical in the medulla; type 5—undifferentiated cells that are typical in the medulla; type 6—large medullary cells that are found around and in the Hassall corpuscles.

The hemopoietic cells include three different types of lymphoid cells: (1) subcapsular cells; (2) cortical cells; and (3) medullary cells.

Thymic accessory cells include macrophages that secrete a thymocyte-differentiating factor that is mitogenic and induces functional maturation of the thymocyte; interdigitating cells, which have a role in determining which T-cell precursors are activated (helper or killer) during an immunological challenge; and myoid cells which appear to express acetylcholine receptors and have a possible role in myasthenia gravis, and may have a role in expelling thymocytes from the thymus gland.

Cells of the thymus appear to express acetylcholine receptors. For example, cholinergic receptors have bound found on the epithelial cells of the thymus. The thymus appears to also receive neuronal innervation from the hypothalamus, which may influence thymic hormones and the immune system in general.

Lymphocytes originate from haemocytoblasts (stem cells) in red bone marrow. The lymphocytes appear to be attracted to the thymus by chemotactic factors produced by epithelial cells. Those lymphocytes that enter the thymus mature and develop into activated T-lymphocytes or activated T-cells. The activated T-cells are able to respond to antigens encountered elsewhere in the body. The T-cells can divide into two groups: (1) a group that enters the blood, some of which remain in circulation and some lodge in other lymphoid tissue; and (2) a group that remains in the thymus gland and are the source of future generations of T-cells.

T cells are believed to carry out three defensive functions: (1) they stimulate the production and growth of antibodies by other lymphocytes; (2) they stimulate the growth and action of phagocytes, which surround and engulf invading viruses and microbes, and (3) they recognize and destroy foreign and abnormal tissue. Thus, the thymus gland plays a critically important role in the body's response to disease invasion. The thymus gland and T cell function play such a pivotal and important role in generating and regulating immune response that a deficiency or imbalance in their function will cause immune system dysfunction.

Autoimmune disorders are diseases caused by an immune response against the body's own cells or tissues. Autoimmune disorders result in destruction of one or more types of body tissues, abnormal growth of an organ or organs, or changes in organ function or functions. The disorders may affect only one organ or tissue type or may affect multiple organs and tissue types. In addition, a person may experience one or more autoimmune disorders at the same time. Organs and tissues commonly affected by autoimmune disorders include blood components such as red blood cells, blood vessels, connective tissues, endocrine glands such as the thyroid or pancreas, muscles, joints, and skin.

Autoimmune disorders can be categorized into two general types: (1) systemic autoimmune diseases (i.e., disorders that damage many organs or tissues), and (2) localized autoimmune diseases (i.e., disorders that damage only a single organ or tissue). However, the effect of localized autoimmune diseases, can be systemic by indirectly affecting other body organs and systems.

Systemic autoimmune diseases include without limitation: rheumatoid arthritis which can affect joints, and possibly lung and skin; lupus, including systemic lupus erythematosus (SLE), which can affect skin, joints, kidneys, heart, brain, red blood cells, as well as other tissues and organs; scleroderma, which can affect skin, intestine, and lungs; Sjogren's syndrome, which can affect salivary glands, tear glands, and joints; Goodpasture's syndrome, which can affect lungs and kidneys; Wegener's granulomatosis, which can affect sinuses, lungs, and kidneys; polymyalgia rheumatica, which can affect large muscle groups, and temporal arteritis/giant cell arteritis, which can affect arteries of the head and neck.

Localized autoimmune diseases include without limitation: Type 1 Diabetes Mellitus, which affects pancreas islets; Hashimoto's thyroiditis and Graves' disease, which affect the thyroid; celiac disease, Crohn's diseases, and ulcerative colitis, which affect the gastrointestinal tract; multiple sclerosis (MS) and Guillain-Barre syndrome, which affect the central nervous system; Addison's disease, which affects the adrenal glands; primary biliary sclerosis, sclerosing cholangitis, and autoimmune hepatitis, which affect the liver; and Raynaud's phenomenon, which can affect the fingers, toes, nose, ears.

The following are additional examples of autoimmune disorders: pernicious anemia; Addison's disease; dermatomyositis; myasthenia gravis (MG); Reiter's syndrome; Pemphigus vulgaris; scleroderma or CREST syndrome; autoimmune hemolytic anemia; autoimmune thrombocytopenic purpura; ankylosing spondylitis; vasculitis; and amyotrophic lateral schlerosis (Lou Gehrig's disease).

Symptoms of autoimmune disorders can vary widely depending on the type of disease. Commonly observed symptoms include fatigue, dizziness, malaise, and fever. Other symptoms that may be observed in one or more autoimmune disorders include chills, weight loss, skin rashes, vasculitis, polyarthralgia, patchy hair loss, oral and nasal sores, lymph-node enlargement, gastric problems, generalized pain, which may be located in the joints in the case of arthritis, enlarged glands, such as the thyroid in the case of Grave's disease, heart palpitations, dermal blisters and lesions, muscle weakness.

Treatment of autoimmune diseases is specific to the disease, and usually concentrates on alleviating or preventing symptoms rather than correcting the underlying cause.

One treatment used in certain autoimmune disorders is administration of cholinesterase inhibitors, which decrease hydrolysis of the neurotransmitter acetylcholine, and thereby increase the amount of acetylcholine available in the synaptic cleft and providing symptomatic relief by increasing stimulation of cholinergic receptors throughout the central and peripheral nervous systems.

Another treatment of autoimmune disorders involves the use of steroids, including corticosteroids, to control or reduce inflammation. Corticosteroids usually are reserved for patients who fail to respond to or do not tolerate anticholinesterase therapy.

A third approach is the administration of immunosuppressive agent, such as azothioprine, to control or reduce the proliferative nature of the immune response. These drugs work by inhibiting the replication of cells and, therefore, also suppress non-immune cells leading to side effects such as anemia.

A fourth approach involves the surgical removal of the thymus gland (i.e., thymectomy).

Another treatment of autoimmune diseases includes the administration of cytokine inhibitors.

Human cytokine overexpression and/or underexpression can result in diseases such as inflammatory bowel disease, arthritis, and systemic lupus erythematosus (Mackay et al., N. Engl J Med, 345(5):340-350, 2001). Arthritis is a common chronic inflammatory and destructive arthropathy due to the overexpression of tumor necrosis factor alpha (TNF-alpha) and/or underexpression of Interleukin-1 (IL-1) receptor antagonist resulting in a cell-mediated immune response causing inflammation and joint damage (Mackay et al., supra; Choy et al., N. Engl. J. Med., 344(12):907-916, 2001).

Cytokine inhibitors include soluble human cytokine receptor proteins (e.g., etanercept), monoclonal antibodies (e.g., rituxamab, infliximab, D2E7, and nerelimomab), and cytokine receptor blockers (e.g., interleukin 1 receptor antagonist). Such inhibitors have been reported to be effective in treating arthritis (Choy et al., supra), asthma (Xolair package insert, Genentech, 2003), and type 1 diabetes mellitus (Herold et al., N. Engl. J. Med., 346(22):1692-1698, 2002). Cytokine inhibitors, specifically monoclonal antibodies, are unique as these agents target specific antigens that grow on the surface of cells (e.g., cancer cells). Radioimmunotherapy consists of a radioactive substance linked to an antibody. This combination provides a targeted delivery (monoclonal antibody) and treatment (radioactive substance) for a specific disease.

Botulinum Toxin

The genus *Clostridium* has more than one hundred and twenty seven species, grouped according to their morphology and functions. The anaerobic, gram positive bacterium *Clostridium botulinum* produces a potent polypeptide neurotoxin, botulinum toxin, which causes a neuroparalytic illness in humans and animals referred to as botulism. The spores of *Clostridium botulinum* are found in soil and can grow in improperly sterilized and sealed food containers of home based canneries, which are the cause of many of the cases of botulism. The effects of botulism typically appear 18 to 36 hours after eating the foodstuffs infected with a *Clostridium botulinum* culture or spores. The botulinum toxin can apparently pass unattenuated through the lining of the gut and attack peripheral motor neurons. Symptoms of botulinum toxin intoxication can progress from difficulty walking, swallowing, and speaking to paralysis of the respiratory muscles and death.

Botulinum toxin type A is the most lethal natural biological agent known to man. About 50 picograms of a commercially available botulinum toxin type A (purified neurotoxin complex)[1] is a LD50 in mice (i.e. 1 unit). One unit of BOTOX® contains about 50 picograms (about 56 attomoles) of botulinum toxin type A complex. Interestingly, on a molar basis, botulinum toxin type A is about 1.8 billion times more lethal than diphtheria, about 600 million times more lethal than sodium cyanide, about 30 million times more lethal than cobra toxin and about 12 million times more lethal than cholera. Singh, *Critical Aspects of Bacterial Protein Toxins*, pages 63-84 (chapter 4) of Natural Toxins II, edited by B. R. Singh et al., Plenum Press, New York (1976) (where the stated LD50 of botulinum toxin type A of 0.3 ng equals 1 U is corrected for the fact that about 0.05 ng of BOTOX® equals 1 unit). One unit (U) of botulinum toxin is defined as the LD50 upon intraperitoneal injection into female Swiss Webster mice weighing 18 to 20 grams each.

[1] Available from Allergan, Inc., of Irvine, Calif. under the tradename BOTOX® in 100 unit vials)

Seven generally immunologically distinct botulinum neurotoxins have been characterized, these being respectively botulinum neurotoxin serotypes A, B, C1, D, E, F and G each of which is distinguished by neutralization with type-specific antibodies. The different serotypes of botulinum toxin vary in the animal species that they affect and in the severity and duration of the paralysis they evoke. For example, it has been determined that botulinum toxin type A is 500 times more potent, as measured by the rate of paralysis produced in the rat, than is botulinum toxin type B. Additionally, botulinum toxin type B has been determined to be non-toxic in primates at a dose of 480 U/kg which is about 12 times the primate LD50 for botulinum toxin type A. Moyer E et al., *Botulinum Toxin Type B: Experimental and Clinical Experience*, being chapter 6, pages 71-85 of "Therapy With Botulinum Toxin", edited by Jankovic, J. et al. (1994), Marcel Dekker, Inc. Botulinum toxin apparently binds with high affinity to cholinergic motor neurons, is translocated into the neuron and blocks the release of acetylcholine. Additional uptake can take place through low affinity receptors, as well as by phagocytosis and pinocytosis.

Regardless of serotype, the molecular mechanism of toxin intoxication appears to be similar and to involve at least three steps or stages. In the first step of the process, the toxin binds to the presynaptic membrane of the target neuron through a specific interaction between the heavy chain, H chain, and a cell surface receptor; the receptor is thought to be different for each type of botulinum toxin and for tetanus toxin. The carboxyl end segment of the H chain, HC, appears to be important for targeting of the toxin to the cell surface.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This step is thought to be mediated by the amino end segment of the H chain, HN, which triggers a conformational change of the toxin in response to a pH of about 5.5 or lower. Endosomes are known to possess a proton pump which decreases intra-endosomal pH. The conformational shift exposes hydrophobic residues in the toxin, which permits the toxin to embed itself in the endosomal membrane. The toxin (or at a minimum the light chain) then translocates through the endosomal membrane into the cytoplasm.

The last step of the mechanism of botulinum toxin activity appears to involve reduction of the disulfide bond joining the heavy chain, H chain, and the light chain, L chain. The entire toxic activity of botulinum and tetanus toxins is contained in the L chain of the holotoxin; the L chain is a zinc (Zn++) endopeptidase which selectively cleaves proteins essential for recognition and docking of neurotransmitter-containing vesicles with the cytoplasmic surface of the plasma membrane, and fusion of the vesicles with the plasma membrane. Tetanus neurotoxin, botulinum toxin types B, D, F, and G cause degradation of synaptobrevin (also called vesicle-associated membrane protein (VAMP)), a synaptosomal membrane protein. Most of the VAMP present at the cytoplasmic surface of the synaptic vesicle is removed as a result of any one of these cleavage events. Botulinum toxin serotype A and E cleave SNAP-25. Botulinum toxin serotype C1 was originally thought to cleave syntaxin, but was found to cleave syntaxin and SNAP-25. Each of the botulinum toxins specifically cleaves a different bond, except botulinum toxin type B (and tetanus toxin) which cleave the same bond. Each of these cleavages block the process of vesicle-membrane docking, thereby preventing exocytosis of vesicle content.

Botulinum toxins have been used in clinical settings for the treatment of neuromuscular disorders characterized by hyperactive skeletal muscles (i.e. motor disorders). In 1989 a botulinum toxin type A complex has been approved by the U.S. Food and Drug Administration for the treatment of blepharospasm, strabismus and hemifacial spasm. Subsequently, a botulinum toxin type A was also approved by the FDA for the treatment of cervical dystonia and for the treatment of glabellar lines, and a botulinum toxin type B was approved for the treatment of cervical dystonia. Non-type A botulinum toxin serotypes apparently have a lower potency and/or a shorter duration of activity as compared to botulinum toxin type A. Clinical effects of peripheral intramuscular botulinum toxin type A are usually seen within one week of injection. The typical duration of symptomatic relief from a single intramuscular injection of botulinum toxin type A averages about three months, although significantly longer periods of therapeutic activity have been reported.

Although all the botulinum toxins serotypes apparently inhibit release of the neurotransmitter acetylcholine at the neuromuscular junction, they do so by affecting different neurosecretory proteins and/or cleaving these proteins at different sites. For example, botulinum types A and E both cleave the 25 kiloDalton (kD) synaptosomal associated protein (SNAP-25), but they target different amino acid sequences within this protein. Botulinum toxin types B, D, F and G act on vesicle-associated protein (VAMP, also called synaptobrevin), with each serotype cleaving the protein at a different site. Finally, botulinum toxin type C1 has been shown to cleave both syntaxin and SNAP-25. These differences in mechanism of action may affect the relative potency and/or duration of action of the various botulinum toxin serotypes. Apparently, a substrate for a botulinum toxin can be found in a variety of different cell types. See e.g. *Biochem J* 1; 339 (pt 1):159-65:1999, and *Mov Disord*, 10(3):376:1995 (pancreatic islet B cells contains at least SNAP-25 and synaptobrevin).

The molecular weight of the botulinum toxin protein molecule, for all seven of the known botulinum toxin serotypes, is about 150 kD. Interestingly, the botulinum toxins are released by *Clostridial bacterium* as complexes comprising the 150 kD botulinum toxin protein molecule along with associated non-toxin proteins. Thus, the botulinum toxin type A complex can be produced by *Clostridial bacterium* as 900 kD, 500 kD and 300 kD forms. Botulinum toxin types B and C1 is apparently produced as only a 700 kD or 500 kD complex. Botulinum toxin type D is produced as both 300 kD and 500 kD complexes. Finally, botulinum toxin types E and F are produced as only approximately 300 kD complexes. The complexes (i.e. molecular weight greater than about 150 kD) are believed to contain a non-toxin hemaglutinin protein and a non-toxin and non-toxic nonhemaglutinin protein. These two non-toxin proteins (which along with the botulinum toxin molecule comprise the relevant neurotoxin complex) may act to provide stability against denaturation to the botulinum toxin molecule and protection against digestive acids when toxin is ingested. Additionally, it is possible that the larger (greater than about 150 kD molecular weight) botulinum toxin complexes may result in a slower rate of diffusion of the botulinum toxin away from a site of intramuscular injection of a botulinum toxin complex.

In vitro studies have indicated that botulinum toxin inhibits potassium cation induced release of both acetylcholine and norepinephrine from primary cell cultures of brainstem tissue. Additionally, it has been reported that botulinum toxin inhibits the evoked release of both glycine and glutamate in primary cultures of spinal cord neurons and that in brain synaptosome preparations botulinum toxin inhibits the release of each of the neurotransmitters acetylcholine, dopamine, norepinephrine (Habermann E., et al., *Tetanus Toxin and Botulinum A and C Neurotoxins Inhibit Noradrenaline Release From Cultured Mouse Brain*, J Neurochem 51(2); 522-527:1988) CGRP, substance P and glutamate (Sanchez-Prieto, J., et al., *Botulinum Toxin A Blocks Glutamate Exocytosis From Guinea Pig Cerebral Cortical Synaptosomes*, Eur J. Biochem 165; 675-681:1897. Thus, when adequate concentrations are used, stimulus-evoked release of most neurotransmitters is blocked by botulinum toxin. See e.g. Pearce, L. B., *Pharmacologic Characterization of Botulinum Toxin For Basic Science and Medicine*, Toxicon 35(9); 1373-1412 at 1393; Bigalke H., et al., *Botulinum A Neurotoxin Inhibits Non-Cholinergic Synaptic Transmission in Mouse Spinal Cord Neurons in Culture*, Brain Research 360; 318-324:1985; Habermann E., *Inhibition by Tetanus and Botulinum A Toxin of the release of [3H]Noradrenaline and [3H]GABA From Rat Brain Homogenate*, Experientia 44; 224-226:1988, Bigalke H., et al., *Tetanus Toxin and Botulinum A Toxin Inhibit Release and Uptake of Various Transmitters, as Studied with Particulate Preparations From Rat Brain and Spinal Cord*, Naunyn-Schmiedeberg's Arch Pharmacol 316; 244-251:1981, and; Jankovic J. et al., *Therapy With Botulinum Toxin*, Marcel Dekker, Inc., (1994), page 5.

Botulinum toxin type A can be obtained by establishing and growing cultures of *Clostridium botulinum* in a fermenter and then harvesting and purifying the fermented mixture in accordance with known procedures. All the botulinum toxin serotypes are initially synthesized as inactive single chain proteins which must be cleaved or nicked by proteases to become neuroactive. The bacterial strains that make botulinum toxin serotypes A and G possess endogenous proteases and serotypes A and G can therefore be recovered from bacterial cultures in predominantly their active form. In contrast, botulinum toxin serotypes C1, D and E are synthesized by nonproteolytic strains and are therefore typically unactivated when recovered from culture. Serotypes B and F are produced by both proteolytic and nonproteolytic strains and therefore can be recovered in either the active or inactive form. However, even the proteolytic strains that produce, for example, the botulinum toxin type B serotype only cleave a portion of the toxin produced. The exact proportion of nicked to unnicked molecules depends on the length of incubation and the temperature of the culture. Therefore, a certain percentage of any preparation of, for example, the botulinum toxin type B toxin is likely to be inactive, possibly accounting for the known significantly lower potency of botulinum toxin type B as compared to botulinum toxin type A. The presence of inactive botulinum toxin molecules in a clinical preparation will contribute to the overall protein load of the preparation, which has been linked to increased antigenicity, without contributing to its clinical efficacy. Additionally, it is known that botulinum toxin type B has, upon intramuscular injection, a shorter duration of activity and is also less potent than botulinum toxin type A at the same dose level.

High quality crystalline botulinum toxin type A can be produced from the Hall A strain of *Clostridium botulinum* with characteristics of $\geq 3 \times 10^7$ U/mg, an $A_{260}/A_{278}$ of less than 0.60 and a distinct pattern of banding on gel electrophoresis. The known Shantz process can be used to obtain crystalline botulinum toxin type A, as set forth in Shantz, E. J., et al, *Properties and use of Botulinum toxin and Other Microbial Neurotoxins in Medicine*, Microbiol Rev. 56; 80-99:1992. Generally, the botulinum toxin type A complex can be isolated and purified from an anaerobic fermentation by cultivating *Clostridium botulinum* type A in a suitable medium. The known process can also be used, upon separation out of the non-toxin proteins, to obtain pure botulinum toxins, such as for example: purified botulinum toxin type A with an approximately 150 kD molecular weight with a specific potency of $1\text{-}2\times 10^8$ LD50 U/mg or greater; purified botulinum toxin type B with an approximately 156 kD molecular weight with a specific potency of $1\text{-}2\times 10^8$ LD50 U/mg or greater, and; purified botulinum toxin type F with an approximately 155 kD molecular weight with a specific potency of $1\text{-}2\times 10^7$ LD50 U/mg or greater.

Botulinum toxins and/or botulinum toxin complexes can be obtained from List Biological Laboratories, Inc., Campbell, Calif.; the Centre for Applied Microbiology and Research, Porton Down, U.K.; Wako (Osaka, Japan), Metabiologics (Madison, Wis.) as well as from Sigma Chemicals of St Louis, Mo. Pure botulinum toxin can also be used to prepare a pharmaceutical composition.

As with enzymes generally, the biological activities of the botulinum toxins (which are intracellular peptidases) is dependant, at least in part, upon their three dimensional conformation. Thus, botulinum toxin type A is detoxified by heat, various chemicals surface stretching and surface drying. Additionally, it is known that dilution of the toxin complex obtained by the known culturing, fermentation and purification to the much, much lower toxin concentrations used for pharmaceutical composition formulation results in rapid detoxification of the toxin unless a suitable stabilizing agent is present. Dilution of the toxin from milligram quantities to a solution containing nanograms per milliliter presents significant difficulties because of the rapid loss of specific toxicity upon such great dilution. Since the toxin may be used months or years after the toxin containing pharmaceutical composition is formulated, the toxin can stabilized with a stabilizing agent such as albumin and gelatin.

A commercially available botulinum toxin containing pharmaceutical composition is sold under the trademark BOTOX® (available from Allergan, Inc., of Irvine, Calif.). BOTOX® consists of a purified botulinum toxin type A complex, albumin and sodium chloride packaged in sterile, vacuum-dried form. The botulinum toxin type A is made from a culture of the Hall strain of *Clostridium botulinum* grown in a medium containing N-Z amine and yeast extract. The botulinum toxin type A complex is purified from the culture solution by a series of acid precipitations to a crystalline complex consisting of the active high molecular weight toxin protein and an associated hemagglutinin protein. The crystalline complex is re-dissolved in a solution containing saline and albumin and sterile filtered (0.2 microns) prior to vacuum-drying. The vacuum-dried product is stored in a freezer at or below −5° C. BOTOX® can be reconstituted with sterile, non-preserved saline prior to intramuscular injection. Each vial of BOTOX® contains about 100 units (U) of *Clostridium botulinum* toxin type A purified neurotoxin complex, 0.5 milligrams of human serum albumin and 0.9 milligrams of sodium chloride in a sterile, vacuum-dried form without a preservative.

To reconstitute vacuum-dried BOTOX®, sterile normal saline without a preservative; (0.9% Sodium Chloride Injection) is used by drawing up the proper amount of diluent in the appropriate size syringe. Since BOTOX® may be denatured by bubbling or similar violent agitation, the diluent is gently injected into the vial. For sterility reasons BOTOX® is preferably administered within four hours after the vial is removed from the freezer and reconstituted. During these four hours, reconstituted BOTOX® can be stored in a refrigerator at about 2° C. to about 8° C. Reconstituted, refrigerated BOTOX® has been reported to retain its potency for at least about two weeks. *Neurology*, 48:249-53:1997.

It has been reported that botulinum toxin type A has been used in clinical settings as follows:

(1) about 75-125 units of BOTOX® per intramuscular injection (multiple muscles) to treat cervical dystonia;

(2) 5-10 units of BOTOX® per intramuscular injection to treat glabellar lines (brow furrows) (5 units injected intramuscularly into the procerus muscle and 10 units injected intramuscularly into each corrugator supercihii muscle);

(3) about 30-80 units of BOTOX® to treat constipation by intrasphincter injection of the puborectalis muscle;

(4) about 1-5 units per muscle of intramuscularly injected BOTOX® to treat blepharospasm by injecting the lateral pre-tarsal orbicularis oculi muscle of the upper lid and the lateral pre-tarsal orbicularis oculi of the lower lid.

(5) to treat strabismus, extraocular muscles have been injected intramuscularly with between about 1-5 units of BOTOX®, the amount injected varying based upon both the size of the muscle to be injected and the extent of muscle paralysis desired (i.e. amount of diopter correction desired).

(6) to treat upper limb spasticity following stroke by intramuscular injections of BOTOX® into five different upper limb flexor muscles, as follows:

(a) flexor digitorum profundus: 7.5 U to 30 U
(b) flexor digitorum sublimus: 7.5 U to 30 U
(c) flexor carpi ulnaris: 10 U to 40 U
(d) flexor carpi radialis: 15 U to 60 U
(e) biceps brachii: 50 U to 200 U. Each of the five indicated muscles has been injected at the same treatment session, so that the patient receives from 90 U to 360 U of upper limb flexor muscle BOTOX® by intramuscular injection at each treatment session.

(7) to treat migraine, pericranial injected (injected symmetrically into glabellar, frontalis and temporalis muscles) injection of 25 U of BOTOX® has showed significant benefit as a prophylactic treatment of migraine compared to vehicle as measured by decreased measures of migraine frequency, maximal severity, associated vomiting and acute medication use over the three month period following the 25 U injection.

Recent studies have demonstrated that botulinum neurotoxin can inhibit insulin secretion, and thus may have a role in the control of insulin exocytosis and metabolic control (Huang et al., Mol. Endocrinol. 12(7):1060-70, 1998).

It is known that botulinum toxin type A can have an efficacy for up to 12 months (*European J. Neurology* 6 (Supp 4): S111-S1150:1999), and in some circumstances for as long as 27 months, when used to treat glands, such as in the treatment of hyperhydrosis. See e.g. Bushara K., *Botulinum toxin and rhinorrhea*, Otolaryngol Head Neck Surg 1996; 114(3):507, and *The Lalyngoscope* 109:1344-1346:1999. However, the usual duration of an intramuscular injection of Botox® is typically about 3 to 4 months.

The success of botulinum toxin type A to treat a variety of clinical conditions has led to interest in other botulinum toxin serotypes. Two commercially available botulinum type A preparations for use in humans are BOTOX® available from Allergan, Inc., of Irvine, Calif., and Dysport® available from Beaufour Ipsen, Porton Down, England. A Botulinum toxin type B preparation (MyoBloc®) is available from Elan Pharmaceuticals of San Francisco, Calif.

In addition to having pharmacologic actions at the peripheral location, botulinum toxins may also have inhibitory effects in the central nervous system. Work by Weigand et al, *Nauny-Schmiedeberg's Arch. Pharmacol.* 1976; 292, 161-165, and Habermann, *Nauny-Schmiedeberg's Arch. Pharmacol.* 1974; 281, 47-56 showed that botulinum toxin is able to ascend to the spinal area by retrograde transport. As such, a botulinum toxin injected at a peripheral location, for example intramuscularly, may be retrograde transported to the spinal cord.

U.S. Pat. No. 5,989,545 discloses that a modified clostridial neurotoxin or fragment thereof, preferably a botulinum toxin, chemically conjugated or recombinantly fused to a particular targeting moiety can be used to treat pain by administration of the agent to the spinal cord.

A botulinum toxin has also been proposed for or has been used to treat otitis media of the ear (U.S. Pat. No. 5,766,605), inner ear disorders (U.S. Pat. Nos. 6,265,379; 6,358,926), tension headache, (U.S. Pat. No. 6,458,365), migraine headache pain (U.S. Pat. No. 5,714,468), post-operative pain and visceral pain (U.S. Pat. No. 6,464,986), hair growth and hair retention (U.S. Pat. No. 6,299,893), psoriasis and dermatitis (U.S. Pat. No. 5,670,484), injured muscles (U.S. Pat. No. 6,423,319) various cancers (U.S. Pat. No. 6,139,845), smooth muscle disorders (U.S. Pat. No. 5,437,291), and neurogenic inflammation (U.S. Pat. No. 6,063,768). Controlled release toxin implants are known (see e.g. U.S. Pat. Nos. 6,306,423 and 6,312,708) as is transdermal botulinum toxin administration (U.S. patent application Ser. No. 10/194,805).

Additionally, a botulinum toxin may have an effect to reduce induced inflammatory pain in a rat formalin model. Aoki K., et al, *Mechanisms of the antinociceptive effect of subcutaneous Botox: Inhibition of peripheral and central nociceptive processing*, Cephalalgia 2003 September; 23(7): 649. Furthermore, it has been reported that botulinum toxin nerve blockage can cause a reduction of epidermal thickness. Li Y., et al., *Sensory and motor denervation influences epidermal thickness in rat foot glabrous skin*, Exp Neurol 1997; 147:452-462 (see page 459). Finally, it is known to administer a botulinum toxin to the foot to treat excessive foot sweating (Katsambas A., et al., *Cutaneous diseases of the foot: Unapproved treatments*, Clin Dermatol 2002 November-December; 20(6):689-699; Sevim, S., et al., *Botulinum toxin-A therapy for palmar and plantar hyperhidrosis*, Acta Neurol Belg 2002 December; 102(4):167-70), spastic toes (Suputtitada, A., *Local botulinum toxin type A injections in the treatment of spastic toes*, Am J Phys Med Rehabil 2002 October; 81(10):770-5), idiopathic toe walking (Tacks, L., et al., *Idiopathic toe walking: Treatment with botulinum toxin A injection*, Dev Med Child Neurol 2002; 44(Suppl 91):6), and foot dystonia (Rogers J., et al., *Injections of botulinum toxin A in foot dystonia*, Neurology 1993 April; 43(4 Suppl 2)).

Tetanus toxin, as wells as derivatives (i.e. with a non-native targeting moiety), fragments, hybrids and chimeras thereof can also have therapeutic utility. The tetanus toxin bears many similarities to the botulinum toxins. Thus, both the tetanus toxin and the botulinum toxins are polypeptides made by closely related species of *Clostridium* (*Clostridium tetani* and *Clostridium botulinum*, respectively). Additionally, both the tetanus toxin and the botulinum toxins are dichain proteins composed of a light chain (molecular weight about 50 kD) covalently bound by a single disulfide bond to a heavy chain (molecular weight about 100 kD). Hence, the molecular weight of tetanus toxin and of each of the seven botulinum toxins (non-complexed) is about 150 kD. Furthermore, for both the tetanus toxin and the botulinum toxins, the light chain bears the domain which exhibits intracellular biological (protease) activity, while the heavy chain comprises the receptor binding (immunogenic) and cell membrane translocational domains.

Further, both the tetanus toxin and the botulinum toxins exhibit a high, specific affinity for gangliocide receptors on the surface of presynaptic cholinergic neurons. Receptor mediated endocytosis of tetanus toxin by peripheral cholinergic neurons results in retrograde axonal transport, blocking of the release of inhibitory neurotransmitters from central synapses and a spastic paralysis. Contrarily, receptor mediated endocytosis of botulinum toxin by peripheral cholinergic neurons results in little if any retrograde transport, inhibition of acetylcholine exocytosis from the intoxicated peripheral motor neurons and a flaccid paralysis.

Finally, the tetanus toxin and the botulinum toxins resemble each other in both biosynthesis and molecular architecture. Thus, there is an overall 34% identity between the protein sequences of tetanus toxin and botulinum toxin type A, and a sequence identity as high as 62% for some functional domains. Binz T. et al., *The Complete Sequence of Botulinum Neurotoxin Type A and Comparison with Other Clostridial Neurotoxins*, J Biological Chemistry 265(16); 9153-9158: 1990.

Acetylcholine

Typically only a single type of small molecule neurotransmitter is released by each type of neuron in the mammalian nervous system, although there is evidence which suggests that several neuromodulators can be released by the same neuron. The neurotransmitter acetylcholine is secreted by neurons in many areas of the brain, but specifically by the large pyramidal cells of the motor cortex, by several different neurons in the basal ganglia, by the motor neurons that innervate the skeletal muscles, by the preganglionic neurons of the autonomic nervous system (both sympathetic and parasympathetic), by the bag 1 fibers of the muscle spindle fiber, by the postganglionic neurons of the parasympathetic nervous system, and by some of the postganglionic neurons of the sympathetic nervous system. Essentially, only the postganglionic sympathetic nerve fibers to the sweat glands, the piloerector muscles and a few blood vessels are cholinergic as most of the postganglionic neurons of the sympathetic nervous system secret the neurotransmitter norepinephine. In most instances acetylcholine has an excitatory effect. However, acetylcholine is known to have inhibitory effects at some of the peripheral parasympathetic nerve endings, such as inhibition of heart rate by the vagal nerve.

The efferent signals of the autonomic nervous system are transmitted to the body through either the sympathetic nervous system or the parasympathetic nervous system. The preganglionic neurons of the sympathetic nervous system extend from preganglionic sympathetic neuron cell bodies located in the intermediolateral horn of the spinal cord. The preganglionic sympathetic nerve fibers, extending from the cell body, synapse with postganglionic neurons located in either a paravertebral sympathetic ganglion or in a prevertebral ganglion. Since, the preganglionic neurons of both the sympathetic and parasympathetic nervous system are cholinergic, application of acetylcholine to the ganglia will excite both sympathetic and parasympathetic postganglionic neurons.

Acetylcholine activates two types of receptors, muscarinic and nicotinic receptors. The muscarinic receptors are found in all effector cells stimulated by the postganglionic, neurons of the parasympathetic nervous system as well as in those stimulated by the postganglionic cholinergic neurons of the sympathetic nervous system. The nicotinic receptors are found in the adrenal medulla, as well as within the autonomic ganglia, that is on the cell surface of the postganglionic neuron at the synapse between the preganglionic and postganglionic neurons of both the sympathetic and parasympathetic systems. Nicotinic receptors are also found in many nonautonomic nerve endings, for example in the membranes of skeletal muscle fibers at the neuromuscular junction.

Acetylcholine is released from cholinergic neurons when small, clear, intracellular vesicles fuse with the presynaptic neuronal cell membrane. A wide variety of non-neuronal secretory cells, such as, adrenal medulla (as well as the PC12 cell line) and pancreatic islet cells release catecholamines and parathyroid hormone, respectively, from large dense-core vesicles. The PC12 cell line is a clone of rat pheochromocytoma cells extensively used as a tissue culture model for studies of sympathoadrenal development. Botulinum toxin inhibits the release of both types of compounds from both types of cells in vitro, permeabilized (as by electroporation) or by direct injection of the toxin into the denervated cell. Botulinum toxin is also known to block release of the neurotransmitter glutamate from cortical synaptosomes cell cultures.

A neuromuscular junction is formed in skeletal muscle by the proximity of axons to muscle cells. A signal transmitted through the nervous system results in an action potential at the terminal axon, with activation of ion channels and resulting release of the neurotransmitter acetylcholine from intraneuronal synaptic vesicles, for example at the motor endplate of the neuromuscular junction. The acetylcholine crosses the extracellular space to bind with acetylcholine receptor proteins on the surface of the muscle end plate. Once sufficient binding has occurred, an action potential of the muscle cell causes specific membrane ion channel changes, resulting in muscle cell contraction. The acetylcholine is then released from the muscle cells and metabolized by cholinesterases in the extracellular space. The metabolites are recycled back into the terminal axon for reprocessing into further acetylcholine.

U.S. Pat. No. 6,585,993 discloses a controlled release neurotoxin system. U.S. Pat. No. 6,506,399 discloses a biodegradable botulinum toxin implant. U.S. Pat. No. 6,383,509 discloses a biodegradable neurotoxin implant. U.S. Pat. No. 6,312,708 discloses a botulinum toxin implant. U.S. Pat. No. 6,306,423 discloses a neurotoxin implant Thus, there remains a need for new compositions and methods which may be used to treat autoimmune disorders.

SUMMARY

The present invention addresses this need and provides new compositions and methods that provide effective relief of one or more autoimmune disorders.

In one embodiment, a method for treating an autoimmune disorder comprises a step of administering a Clostridial neurotoxin, such as a botulinum toxin, to a location in proximity to the thymus gland of a patient that has an autoimmune disorder. In certain embodiments, the Clostridial neurotoxin is a botulinum toxin type A which is injected directly into the thymus gland. In this embodiment, the method can also comprise a step of administering a cytokine inhibitor to the patient.

In another embodiment, a method for treating an autoimmune disorder comprises administering a therapeutically effective amount of a Clostridial neurotoxin, such as a botulinum toxin, and a therapeutically effective amount of a cytokine inhibitor to a patient that has an autoimmune disorder. The combined administration provides synergistic effects not observed by the administration of either agent alone. In this embodiment, the method can also comprise a step of administering the neurotoxin to the thymus gland of the patient.

Compositions for treating an autoimmune disorder are also disclosed. Such compositions may be suitable for administration to or near the thymus gland of a patient with an autoimmune disorder. The compositions may comprise a combination of one or more Clostridial neurotoxins and one or more cytokine inhibitors.

Each and every feature described herein, and each and every combination of two or more of such features, is included within the scope of the present invention provided that the features included in such a combination are not mutually inconsistent. In addition, any feature or combination of features may be specifically excluded from any embodiment of the present invention.

Additional aspects and advantages of the present invention are set forth in the following description and claims, particularly when considered in conjunction with the accompanying examples.

DEFINITIONS

The following definitions apply herein.

"About" means plus or minus ten percent of the value so qualified.

"Biocompatible" means that there is no significant inflammatory or antigenic response from administration of the composition.

"Biologically active compound" means a compound which can effect a beneficial change in the subject to which it is administered. For example, "biologically active compounds" include neurotoxins.

"Effective amount" as applied to the biologically active compound means that amount of the compound which is generally sufficient to effect a desired change in the subject. For example, where the desired effect is a reduction in an autoimmune disorder symptom, an effective amount of the compound is that amount which causes at least a substantial reduction of the autoimmune disorder symptom, and without resulting in significant toxicity.

"Effective amount" as applied to a non-active ingredient constituent of an injectable composition (such as a carrier used for mixing with a botulinum toxin) refers to that amount of the non-active ingredient constituent which is sufficient to positively influence the release and/or activity of the active ingredient when administered to an individual. This "effective amount" can be determined based on the teaching in this specification and the general knowledge in the art.

"Neurotoxin" means an agent which can interrupt nerve impulse transmission across a neuromuscular or neuroglandular junction, block or reduce neuronal exocytosis of a neurotransmitter or alter the action potential at a sodium channel voltage gate of a neuron. Examples of neurotoxins include botulinum toxins, tetanus toxins, saxitoxins, and tetrodotoxin.

"Treatment" means any treatment of a disease in a mammal, and includes: (i) preventing the disease from occurring or; (ii) inhibiting the disease, i.e., arresting its development; (iii) relieving the disease, i.e., reducing the incidence of symptoms of or causing regression of the disease.

"Implants" refer to substantially non-liquid drug delivery devices. Implants may include a polymeric component, such as a biodegradable or non-biodegradable polymer, associated with a neurotoxin. The implants may be solid, semi-solid, or visco-elastic. Implants are generally larger than microspheres.

"Microspheres" refers to a polymer or combinations of polymers made into bodies or elements of various sizes. The microspheres can be in any shape, although they are often in substantially spherical shape.

"Biodegradable" microspheres refer to microspheres that are capable of being absorbed by the body, chemically, physiologically, or by other biological means, over a period of time.

"Therapeutic agent" as used herein refers to any substance that provides therapeutic effects to the process of autoimmune disorder treatment or biological or physiological responses to the autoimmune disorder treatment. An example of therapeutic agent is a neurotoxin which is effective in relaxing muscles. One example of a suitable neurotoxin is a neurotoxin produced by Clostridial bacteria, such as *Clostridium beratti*, *Clostridium butyricum*, *Clostridium tetani*, and *Clostridium botulinum*. As described herein, preferred compositions comprise a botulinum toxin component. A botulinum toxin component is a portion of the composition which includes one or more botulinum toxin types selected from the group consisting of botulinum toxin types A, B, C, D, E, F, and G. The botulinum toxin component may comprise a botulinum toxin produced by a Clostridial bacteria, or produced by recombinant technology. The botulinum toxin can be a recombinantly made or a hybrid botulinum toxin. In preferred compositions, the botulinum toxin component comprises a botulinum toxin type A, such as the commercially available botulinum toxin sold under the tradename, BOTOX® (Allergan, Inc., CA).

DESCRIPTION

New methods of treating autoimmune disorders have been invented, as well as compositions for treating autoimmune disorders. The present methods and compositions include a Clostridial neurotoxin that is administered to a patient, such as a human or animal patient, suffering from an autoimmune disorder. As used herein, an autoimmune disorder refers to diseases caused by an immune response against the body's own cells or tissues. The present methods and compositions provide novel ways of treating an autoimmune disorder that can provide reduced side effects and enhanced durations of relief compared to existing therapeutic approaches.

In one embodiment, a method for treating an autoimmune disorder, comprises administering an effective amount of a Clostridial neurotoxin to a location in proximity to a thymus gland of a patient to alleviate at least one symptom of an autoimmune disorder. In certain situations, the administration of the Clostridial neurotoxin is effective in completely treating the autoimmune disorder. By administering the Clostridial neurotoxin to a location in proximity to the thymus gland, it is believed that the neurotoxin can effectively reduce the activity of thymus epithelial cells, and thereby interfere with T cell maturation, immune function, and immune dysfunction.

The Clostridial neurotoxin is administered to a region near the thymus gland. For example, the neurotoxin can be administered to a region spaced away from the thymus gland tissue but close enough to cause the desired alleviation of at least one autoimmune disorder symptom associated with thymus gland activity. While not wishing to be bound by any particular theory or mechanism of action, administration of the Clostridial neurotoxin to a location near the thymus gland can result in the neurotoxin inhibiting acetylcholine release from cholinergic neurons innervating the thymus gland. The inhibition of the acetylcholine release can thus interfere with T cell maturation, as described above. Thus, in one embodiment, the Clostridial neurotoxin is administered to a location near the thymus gland and containing cholinergic neurons innervating the thymus gland. In another embodiment, the Clostridial neurotoxin is administered directly to the thymus gland. For example, as discussed herein the Clostridial neurotoxin, such as a botulinum toxin, can be directly injected into the thymus gland by inserting a needle into the patient so that the needle tip contacts tissue of the thymus gland. When the neurotoxin is not administered directly into the thymus gland, the neurotoxin can be administered at a location spaced away from the thymus gland by a distance ranging from about 5 millimeters to about 50 millimeters from a surface of the thymus gland. In certain embodiments, it may be desirable to administer the neurotoxin to a non-systemic, non-muscular region in the body near the thymus gland.

Locally administering the Clostridial neurotoxin to a location near the thymus gland can provide effective therapy of the autoimmune disorder with reduced side effects associated with conventional therapies. For example, as discussed herein, therapies using cholinesterase inhibitors may be associated with increased muscular hypertension and peripheral and central nervous system activity due to increased amounts of acetylcholine residing in synaptic clefts. Long term steroid and immunosuppressive agent use can result in undesirable side effects since such agents are administered systemically. Thus, this embodiment can provide an effective autoimmune disorder treatment by providing local inhibition of neurotransmitter or peptide release near the thymus gland.

In certain embodiments, the method comprises one or more steps to facilitate location of the thymus gland by the physician performing the administration. For example, an incision may be made in the chest region overlying the thymus gland to provide direct physical access to the thymus gland by a neurotoxin delivery device, such as a needle or cannula configured to pass a neurotoxin containing composition therethrough. Another method may comprise using a thymus visualization device, which may not require making an incision in a chest region of the patient. In certain methods, the neurotoxin is administered without using an electrode, such as electrodes that are used to administer BOTOX® to treat neuromuscular conditions. Other methods of identifying an appropriate administration site or target site can be practiced using routine methods known by persons of ordinary skill in the art.

In another embodiment of the present invention, a method for treating an autoimmune disorder comprises administering an effective amount of a Clostridial neurotoxin and an effective amount of a cytokine inhibitor to a patient suffering from an autoimmune disorder. This combined therapeutic treatment can alleviate one or more symptoms of the autoimmune disorder or completely treat the autoimmune disorder.

In practicing the foregoing method, the Clostridial neurotoxin and the cytokine inhibitor can be administered in amounts that provide a greater relief of the symptom or symptoms compared to the administration of either the Clostridial neurotoxin or the cytokine inhibitor, but not both. Thus, the present combination therapy provides an unexpected therapeutic result not realized by the administration of the Clostridial neurotoxin and cytokine inhibitor separately. In certain embodiments, the Clostridial neurotoxin is administered to the thymus gland of the patient, as discussed herein. In other embodiments, the Clostridial neurotoxin is administered to a region effective in inhibiting neuropeptide release, such as the release of calcitonin gene related peptide (CGRP), glutamate, and substance P, or in inhibiting inflammatory pain. In further embodiments, the Clostridial neurotoxin is administered to a patient in an amount effective in inhibiting neuropeptide mediated inflammation, and the cytokine inhibitor is administered in an amount effective in inhibiting cytokine mediated inflammation.

The cytokine inhibitor that can be administered to the patients include, without limitation, cytokine neutralizers, cytokine receptor blockers, and anti-inflammatory cytokines, or combinations thereof.

Cytokine neutralizers that block or reduce the activity of inflammatory cytokines by preventing the inflammatory cytokine from interacting or binding to its cell-surface receptor. Thus, a cytokine neutralizer in accordance with the disclosure herein includes, without limitation, a soluble receptor fusion protein that can be administered to bind with the inflammatory cytokine, a natural cytokine antagonist, or an antibody, such as monoclonal antibody, or fragment thereof, that recognizes and binds the inflammatory cytokine. Examples of cytokine receptor blockers include cytokine receptor antagonists and antibodies, such as monoclonal antibodies, or fragments thereof, that recognize and bind the cytokine receptor. Anti-inflammatory cytokines can be administered to inhibit the expression of inflammatory cytokines from cytokine expressing cells.

Some specific examples of cytokine inhibitors include pyridinyl imidazoles, bicyclic imidazoles, oxpentifylline, thalidomide, and gabexate mesilate. Additional cytokine inhibitors can be obtained or identified using routine methods known to persons of ordinary skill in the art. For example, potential cytokine inhibitors can be identified using screening assays and comparing the activity of the potential cytokine inhibitor to existing cytokine inhibitors.

For autoimmune disorders that are associated with an inflammatory response, such as asthma, the combination of the Clostridial neurotoxin and monoclonal antibodies for cytokines or cytokine receptors can provide a synergistic reduction in the inflammation associated with the autoimmune disorder. Similar synergistic effects can be observed in the treatment of diabetes. In addition, in situations in which the cytokine inhibitor, such as an antibody, is linked or attached to the neurotoxin, targeted delivery of the neurotoxin can be achieved to provide enhanced synergistic effects to treat the autoimmune disorder.

In the disclosed combination therapies, the site of administration of the neurotoxin and the cytokine inhibitor can vary. For example, both the neurotoxin and cytokine inhibitor can be administered at the same site, or at a different site. In addition, the modes of administration can be the same or different. In certain embodiments, the neurotoxin can be administered to a site in which the patient is experiencing inflammation pain. For example, the neurotoxin can be injected near or in a joint. Or, the neurotoxin can be administered in a site effective in controlling insulin release. The neurotoxin can be administered topically, transdermally, intradermally, subcutaneously, intraglandularly, or intramuscularly. The cytokine inhibitor, when administered separately from the neurotoxin, can be administered in a manner effective to provide systemic delivery of the inhibitor. It may be desirable to administer the cytokine inhibitor intramuscularly or intraperitoneally, however, oral and subcutaneous administration may also be effective.

In practicing the foregoing methods, the Clostridial neurotoxin can be any neurotoxin produced by a Clostridial bacteria or any neurotoxin have an amino acid sequence substantially identical or exactly identical to a neurotoxin produced by a Clostridial bacteria. In certain embodiments, the Clostridial neurotoxin administered to the patient is selected from the group consisting of botulinum toxin types A, B, C, D, E, F, and G. In certain preferred methods, the Clostridial neurotoxin is botulinum toxin type A. Botulinum toxin type A is desirable due to its high potency in humans, ready availability, and known use for inhibiting neurotransmitter release.

Although the present methods and compositions are described with particular reference to botulinum toxins, other neurotoxins may be effective in the present compositions with or without the botulinum toxins, and such other neurotoxins are included within the scope of the present invention. Examples of other Clostridial neurotoxins within the scope of the present invention include neurotoxins made by *Clostridium butyricum* and *Clostridium beratti* species. The present invention also includes the use of (a) Clostridial neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins. These neurotoxin variants may be selected by screening the variants using conventional assays to identify neurotoxins that have the desired physiological effects of inhibiting neurotransmission.

The neurotoxins used in the present methods can be administered to the patient in a variety of forms. For example, in certain embodiments, the neurotoxins is administered in a composition, such as a solution, that comprises a carrier component, such as saline, and the like. In other embodiments, the neurotoxins may be administered by an implant device. The implant device is a non-liquid device that typically comprises a polymeric component. The neurotoxin-containing implants may be biodegradable or non-biodegradable. In other words, the implant may comprise a biodegradable polymer, a non-biodegradable polymer, and combinations thereof. In certain embodiments, the neurotoxin is administered in the form of polymeric microspheres, such as biodegradable microspheres. Implants may also include a pumping mechanism to provide controlled release of the neurotoxin, or the implants may provide a controlled release based on the physiochemical properties of the implants. Examples of potential neurotoxin containing implants, include those implants disclosed the patents identified hereinabove.

The present methods can thus comprise a step of injecting a composition comprising a botulinum toxin component and a carrier component into the patient, placing an implant device comprising a botulinum toxin into the patient, or a combination thereof. In certain embodiments, the Clostridial neurotoxin is administered in a single composition with the cytokine inhibitor. For example, a liquid or polymeric composition containing a therapeutically effective amount of a botulinum neurotoxin and a cytokine inhibitor can be administered to a patient in a single step. In other embodiments, the neurotoxin and cytokine inhibitor are administered in separate compositions, which may be administered to the patient at the same time or at different times. Thus, the present invention also encompasses pharmaceutical compositions comprising a Clostridial neurotoxin and one or more cytokine inhibitors present in a single composition.

Botulinum toxins for use according to the present invention can be stored in lyophilized, vacuum dried form in containers under vacuum pressure or as stable liquids. Prior to lyophilization the botulinum toxin can be combined with pharmaceutically acceptable excipients, stabilizers and/or carriers, such as albumin. The lyophilized material can be reconstituted with saline or water to create a solution or composition containing the botulinum toxin to be administered to the patient.

The amount of the Clostridial neurotoxin in the compositions or administered according to the present methods can vary according to the particular characteristics of the disorder being treated, including its severity and other various patient variables including size, weight, age, and responsiveness to therapy. To guide the practitioner, typically, no less than about 1 unit and no more than about 50 units of a botulinum toxin type A (such as BOTOX®) is administered per injection site (i.e. to the thymus gland or other inflammation site), per patient treatment session. For a botulinum toxin type A such as DYSPORT®, no less than about 2 units and no more about 200 units of the botulinum toxin type A are administered per administration or injection site, per patient treatment session. For a botulinum toxin type B such as MYOBLOC®, no less than about 40 units and no more about 2500 units of the botulinum toxin type B are administered per injection site, per patient treatment session. Less than about 1, 2 or 40 units (of BOTOX®, DYSPORT® and MYOBLOC® respectively) can fail to achieve a desired therapeutic effect, while more than about 50, 200 or 2500 units (of BOTOX®, DYSPORT® and MYOBLOC® respectively) can result in clinically observable and undesired muscle hypotonicity, weakness and/or paralysis.

More preferably: for BOTOX® no less than about 2 units and no more about 20 units of a botulinum toxin type A; for DYSPORT® no less than about 4 units and no more than about 100 units, and; for MYOBLOC®, no less than about 80 units and no more than about 1000 units are, respectively, administered per injection site, per patient treatment session.

Most preferably: for BOTOX® no less than about 5 units and no more about 15 units of a botulinum toxin type A; for DYSPORT® no less than about 20 units and no more than about 75 units, and; for MYOBLOC®, no less than about 200 units and no more than about 750 units are, respectively, administered per injection site, per patient treatment session. It is important to note that there can be multiple injection sites (i.e. a pattern of injections) for each patient treatment session.

Thus, the present methods may comprise administering an amount of a botulinum toxin in a range from about 1 unit to about 50,000 units. The amount of botulinum toxin will vary depending on the type of botulinum toxin, such as the serotype or strain of botulinum toxin, and the amount of the composition to be administered to a patient. In certain methods, botulinum toxin A is administered in an amount ranging from about 10 units to about 2,000 units. In other methods, botulinum toxin type B is administered in an amount ranging from about 100 units to about 30,000 units. Preferably, the present methods comprise administering biologically active botulinum toxins as a therapeutic agent. For example, the present methods do not include administering a botulinum toxoid to the patient.

The present methods can be practiced to treat one or more autoimmune disorders. The autoimmune disorders treatable by the present methods include either or both of system autoimmune diseases or localized autoimmune diseases. Examples of autoimmune disorders treated by the present methods include one or more of any of the following rheumatoid arthritis which can affect joints, and possibly lung and skin; lupus, including systemic lupus erythematosus (SLE), which can affect skin, joints, kidneys, heart, brain, red blood cells, as well as other tissues and organs; scleroderma, which can affect skin, intestine, and lungs; Sjogren's syndrome, which can affect salivary glands, tear glands, and joints; Goodpasture's syndrome, which can affect lungs and kidneys; Wegener's granulomatosis, which can affect sinuses, lungs, and kidneys; polymyalgia rheumatica, which can affect large muscle groups; temporal arteritis/giant cell arteritis, which can affect arteries of the head and neck; Type 1 Diabetes Mellitus, which affects pancreas islets; Hashimoto's thyroiditis and Graves' disease, which affect the thyroid; celiac disease, Crohn's diseases, and ulcerative colitis, which affect the gastrointestinal tract; multiple sclerosis (MS) and Guillain-Barre syndrome, which affect the central nervous system; Addison's disease, which affects the adrenal glands; primary biliary sclerosis, sclerosing cholangitis, and autoimmune hepatitis, which affect the liver; Raynaud's phenomenon, which can affect the fingers, toes, nose, ears; pernicious anemia; Addison's disease; dermatomyositis; myasthenia gravis (MG); Reiter's syndrome; Pemphigus vulgaris; scleroderma or CREST syndrome; autoimmune hemolytic anemia; autoimmune thrombocytopenic purpura; ankylosing spondylitis; vasculitis; and amyotrophic lateral schlerosis (Lou Gehrig's disease).

In certain embodiments, the methods are practiced by administering a Clostridial neurotoxin in proximity to the thymus gland to treat multiple sclerosis, myasthenia gravis, or systemic lupus erythematosus.

The present methods are effective in treating at least one symptom of an autoimmune disorder, including at least one symptom selected from the group consisting of fatigue, dizziness, malaise, fever, chills, weight loss, skin rashes, vasculitis, polyarthralgia, patchy hair loss, oral and nasal sores, lymph-node enlargement, gastric problems, generalized pain, which may be located in the joints in the case of arthritis, enlarged glands, such as the thyroid in the case of Grave's disease, heart palpitations, dermal blisters and lesions, muscle weakness, and combinations thereof.

In addition, the present methods may be effective in treating the cause of the autoimmune disorder by controlling or regulating T cell maturation based on thymus gland activity.

Although examples of routes of administration and dosages are provided, the appropriate route of administration and dosage are generally determined on a case by case basis by the attending physician. Such determinations are routine to one of ordinary skill in the art (see for example, *Harrison's Principles of Internal Medicine* (1998), edited by Anthony Fauci et al., 14th edition, published by McGraw Hill). For example, the route and dosage for administration of a Clostridial neurotoxin according to the present disclosed invention can be selected based upon criteria such as the solubility characteristics of the neurotoxin chosen as well as the intensity and scope of the autoimmune disorder being treated.

Injection of the compositions can be carried out by syringe, catheters, needles and other means for injecting or infusing compositions containing the neurotoxin and/or cytokine inhibitor. As discussed herein, the injection can be practiced with one or more steps of identifying a target site for the injection.

The frequency and the amount injected is determined based on the nature and location of the particular autoimmune disorder being treated. Generally, because of the stable and long lasting character of the neurotoxin injectable composition, multiple injections are not necessary. In certain cases, however, repeated injection may be desired to achieve optimal results. The frequency and the amount of the injection for each particular case is determined by the person of ordinary skill in the art.

Administration of the neurotoxin to the thymus gland, or administration of the neurotoxin in combination with the cytokine inhibitor, provides an initial relief or alleviation of at least one symptom of an autoimmune disorder within about seven days after the administration to the patient. Relief can be obtained for several months or years depending on the mode of administration. For example, a liquid composition containing botulinum toxin type A, such as BOTOX®, can provide relief for about four to about 6 months after administration. An implant that delivers a botulinum toxin type A can provide a therapeutic relief for at least six months, and even for more than a year, such as for three or five years. The synergistic effects provided by the combination therapy of the neurotoxin and cytokine inhibitors can be observed for several months, for example between about one and about 12 months. In certain situations, the neurotoxin effects persist beyond the effects mediated by the cytokine inhibitors.

Thus, in one specific embodiment of the present invention, a method for treating an autoimmune disorder, such as systemic lupus erythematosus, myasthenia gravis, or multiple sclerosis, comprises a step of injecting a therapeutically effective amount of a botulinum toxin type A, such as the compositions available under the tradenames BOTOX® or DYSPORT®, into the thymus gland of a patient that has an autoimmune disorder. The injection of the botulinum toxin into the thymus gland is effective in reducing the activity of the thymus epithelial cells, reducing T cell maturation, immune function, and immune dysfunction.

In another specific embodiment of the present invention, a method for treating an autoimmune disorder, such as systemic lupus erythematosus, arthritis, asthma, and diabetes, comprises a step of administering a therapeutically effective amount of a botulinum toxin type A, such as the compositions available under the tradenames BOTOX® or DYSPORT®, and a therapeutically effective amount of a cytokine inhibitor to a patient that has an autoimmune disorder. The administration of the botulinum toxin and the cytokine inhibitor provides enhanced or synergistic effects for the treatment of the autoimmune disorder.

EXAMPLES

The following non-limiting examples provide those of ordinary skill in the art with specific preferred methods to treat conditions within the scope of the present invention and are not intended to limit the scope of the invention. In the following examples various modes of non-systemic administration of a Clostridial neurotoxin can be carried out.

Example 1

Treatment of Systemic Lupus Erythematosus with a Botulinum Neurotoxin

A 42 year old man diagnosed with systemic lupus erythematosus is treated by injecting 10 units of BOTOX® into the thymus gland (5 units are injected into each lobe of the thymus). After about 1 week, the patient shows a reduced fever, headache, joint pain, and skin rash. Overall, the patient generally feels less fatigued and has a positive outlook. The relief persists for about 4 months.

Six months after his initial treatment, the patient undergoes surgery to receive a biodegradable implant containing botulinum toxin type A. A 1 mg implant is placed 5 mm from the thymus. The implant contains about 200 units of botulinum toxin type A and poly (lactide-co-glycolide) polymer (PLGA). The implant releases the botulinum toxin at a rate of about 2 units per day. The patient reports an improvement similar to the thymus injection of BOTOX® after about 10 days. However, relief from the symptoms persist for 18 months after the surgical procedure.

Example 2

Treatment of Myasthenia Gravis with a Botulinum Neurotoxin

The procedures of Example 1 are followed to treat a female patient diagnosed with Myasthenia Gravis. The patient presents with ptosis, blurred vision, and overall ocular immotility. The treatments successfully prevent the further development of the disorder and the associated muscle weakening of arms, hands, and respiratory system.

Example 3

Treatment of Multiple Sclerosis with a Botulinum Neurotoxin

The procedures of Example 1 are followed to treat a female patient diagnosed with Multiple Sclerosis. The patient presents with blurred vision and ocular pain, as well as limb spasticity. After administering the botulinum toxin type A to the thymus, without administering the botulinum toxin to a muscle, the symptoms are alleviated within about 14 days. The alleviation of the symptoms persists for several months.

Examples 4 to 6

The procedures of Examples 1-3 are repeated for different patients suffering from the same conditions, but by administering a four fold greater amount of DYSPORT available from Ipsen Pharmaceuticals, Paris, France.

Examples 7 to 9

The procedures of Examples 1-3 are repeated for different patients suffering from the same conditions, but by administering an equal amount of purified botulinum toxin type A (e.g., a botulinum toxin type A protein preparation without complexing proteins) available under the name NT 201 from Merz Pharmaceuticals (Frankfurt, Germany).

Examples 10 to 12

The procedures of Examples 1-3 are repeated for different patients suffering from the same conditions, but by administering a fifty fold greater amount of botulinum toxin type B (i.e., MyoBloc available from Solstice Neurosciences, San Diego, Calif.).

Examples 13 to 15

The procedures of Example 1-3 are repeated for different patients suffering from the same condition but by administering therapeutically effective amounts of botulinum toxin type C instead of botulinum toxin type A.

Examples 16 to 18

The procedures of Example 1-3 are repeated for different patients suffering from the same condition but by administering therapeutically effective amounts of botulinum toxin type C instead of botulinum toxin type A.

Examples 19 to 21

The procedures of Example 1-3 are repeated for different patients suffering from the same condition but by administering therapeutically effective amounts of botulinum toxin type D instead of botulinum toxin type A.

Examples 22 to 24

The procedures of Example 1-3 are repeated for different patients suffering from the same condition but by administering therapeutically effective amounts of botulinum toxin type E instead of botulinum toxin type A.

Examples 25 to 27

The procedures of Example 1-3 are repeated for different patients suffering from the same condition but by administering therapeutically effective amounts of botulinum toxin type F instead of botulinum toxin type A.

Examples 28 to 30

The procedures of Example 1-3 are repeated for different patients suffering from the same condition but by administering therapeutically effective amounts of botulinum toxin type G instead of botulinum toxin type A.

Example 31

Treatment of Asthma with a Botulinum Neurotoxin and a Humanized Monoclonal Antibody A 38 year old man suffering from asthma is treated by a combination therapy based on administration of BOTOX® and the monoclonal antibody, omalizumab (Xolair®). The man is treated by injecting 5 units of BOTOX® into nerve fibers responsible for bronchoconstriction, and by injecting 150 mg of Xolair® in a single subcutaneous bolus injection. Immediate relief is provided by the patient's inhaler. The patient reports a reduced number of asthmatic episodes over the following six months.

Example 32

Treatment of Diabetes with a Botulinum Neurotoxin and a Humanized Monoclonal Antibody A 22 year old male with type 1 diabetes mellitus is treated by a combination therapy of administration of a botulinum neurotoxin and the anti-CD3 humanized monoclonal antibody hOKT3gamma1 (Ala-Ala). The patient is administered about 20 units of BOTOX® and antibody injections once a week for six weeks. After about 3 weeks, the symptoms of the diabetes are reduced. The relief persists for about 6 months after initial treatment.

Example 33

Treatment of Arthritis with a Botulinum Neurotoxin and a Cytokine Receptor Blocker A 62 year old male suffering from rheumatoid arthritis is treated by a combination therapy of a botulinum neurotoxin and an interleukin 1 receptor antagonist. The patient is administered 2 units of BOTOX® into each of the joints of his left hand and receives a subcutaneous injection of the antagonist. The patient experiences an overall reduction in joint pain. The reduction of pain in his left hand persists for about 4 months whereas the reduction in joint pain in other regions of his body lasts less than 4 months.

Examples 34 to 36

The procedures of Examples 31-33 are repeated for different patients suffering from the same conditions, but by administering a four fold greater amount of DYSPORT available from Ipsen Pharmaceuticals, Paris, France.

Examples 37 to 39

The procedures of Examples 31-33 are repeated for different patients suffering from the same conditions, but by administering an equal amount of purified botulinum toxin (e.g., a botulinum toxin protein preparation without complexing proteins) available under the name NT 201 from Merz Pharmaceuticals (Frankfurt, Germany).

Examples 40 to 42

The procedures of Examples 31-33 are repeated for different patients suffering from the same conditions, but by administering a fifty fold greater amount of botulinum toxin type B (i.e., MyoBloc available from Solstice Neurosciences, San Diego, Calif.).

Examples 43 to 45

The procedures of Example 31-33 are repeated for different patients suffering from the same condition but by administering therapeutically effective amounts of botulinum toxin type C instead of botulinum toxin type A.

Examples 46 to 48

The procedures of Example 31-33 are repeated for different patients suffering from the same condition but by administering therapeutically effective amounts of botulinum toxin type C instead of botulinum toxin type A.

Examples 49 to 51

The procedures of Example 31-33 are repeated for different patients suffering from the same condition but by administering therapeutically effective amounts of botulinum toxin type D instead of botulinum toxin type A.

Examples 52 to 54

The procedures of Example 31-33 are repeated for different patients suffering from the same condition but by administering therapeutically effective amounts of botulinum toxin type E instead of botulinum toxin type A.

Examples 55 to 57

The procedures of Example 31-33 are repeated for different patients suffering from the same condition but by administering therapeutically effective amounts of botulinum toxin type F instead of botulinum toxin type A.

Examples 58 to 60

The procedures of Example 31-33 are repeated for different patients suffering from the same condition but by administering therapeutically effective amounts of botulinum toxin type G instead of botulinum toxin type A.

Although the present invention has been described in detail with regard to certain preferred compositions and methods, other embodiments, versions, and modifications within the scope of the present invention are possible. For example, a wide variety of neurotoxins can be effectively used in the methods of the present invention. Additionally, the present invention includes local administration methods to alleviate one or more symptoms of an autoimmune disorder wherein two or more neurotoxins, such as two or more botulinum toxins, are administered concurrently or consecutively. For example, botulinum toxin type A can be administered until a loss of clinical response or neutralizing antibodies develop, followed by administration of botulinum toxin type B. Alternately, a combination of any two or more of the botulinum serotypes A-G can be locally administered to control the onset and duration of the desired result. Furthermore, non-neurotoxin compounds can be administered prior to, concurrently with or subsequent to administration of the neurotoxin to proved adjunct effect such as enhanced or a more rapid onset of denervation before the neurotoxin, such as a botulinum toxin, begins to exert its therapeutic effect.

Our invention also includes within its scope the use of a neurotoxin, such as a botulinum toxin, in the preparation of a medicament for the treatment of an autoimmune disorder.

All references, articles, patents, applications and publications set forth above are incorporated herein by reference in their entireties.

Accordingly, the spirit and scope of the following claims should not be limited to the descriptions of the preferred embodiments set forth above.

What is claimed is:

1. A method for treating a non-arthritic autoimmune disorder in a patient in need thereof, the method comprising: administering an effective amount of a Clostridial neurotoxin to a location in proximity to the thymus gland of a patient to alleviate at least one symptom of the non-arthritic autoimmune disorder, thereby treating the non-arthritic autoimmune disorder; wherein the effective amount of a botulinum toxin is that amount which causes alleviation of a symptom of the non-arthritic autoimmune disorder without systemic toxicity resulting.

2. The method of claim 1, wherein the Clostridial neurotoxin is administered to a location containing cholinergic neurons innervating the thymus gland.

3. The method of claim 1, wherein the Clostridial neurotoxin is administered directly to the thymus gland.

4. The method of claim 1, wherein the Clostridial neurotoxin is selected from the group consisting of botulinum toxins types A, B, $C_1$, D, E, F, and G.

5. The method of claim 1, wherein the Clostridial neurotoxin is botulinum toxin type A.

6. The method of claim 1, wherein the botulinum toxin administered is a botulinum toxin type A in an amount from no less than about 1 unit and no more than about 50 units of a botulinum toxin type A per injection site per patient treatment session.

7. The method of claim 1, wherein the botulinum toxin administered is a botulinum toxin type A in an amount from no less than about 2 unit and no more than about 200 units of a botulinum toxin type A per injection site per patient treatment session.

8. The method of claim 1, wherein the botulinum toxin administered is a botulinum toxin type B in an amount from no less than about 40 unit and no more than about 2500 units of a botulinum toxin type B per injection site per patient treatment session.

9. The method of claim 1, wherein the administering comprises a step selected from the group consisting of injecting a composition comprising a botulinum toxin component and a carrier component into the patient, and placing an implant device comprising a botulinum toxin into the patient.

10. The method of claim 1, further comprising administering a cytokine inhibitor to the patient in an amount effective to alleviate at least one symptom of the non-arthritic autoimmune disorder.

11. The method of claim 1, wherein the non-arthritic autoimmune disorder is selected from the group consisting of scleroderma or CREST syndrome, Sjogren's syndrome, Goodpasture's syndrome, Wegener's granulomatosis, temporal arteritis/giant cell arteritis, Type 1 Diabetes Mellitus, Hashimoto's thyroiditis, Graves' disease, celiac disease, Crohn's diseases, ulcerative colitis, multiple sclerosis, Guillain-Barre syndrome, Addison's disease, primary biliary sclerosis, sclerosing cholangitis, autoimmune hepatitis, Raynaud's phenomenon, pernicious anemia, Addison's disease, dermatomyositis, myasthenia gravis, Pemphigus vulgaris, autoimmune hemolytic anemia, autoimmune thrombocytopenic purpura, vasculitis, and amyotrophic lateral schierosis.

12. A method for treating a non-arthritic autoimmune disorder in a patient in need thereof, the method comprising: administering an effective amount of a Clostridial neurotoxin and an effective amount of a cytokine inhibitor to a patient to alleviate at least one symptom of the non-arthritic autoimmune disorder, thereby treating the non-arthritic autoimmune disorder;
   wherein the effective amount of a botulinum toxin is that amount which causes alleviation of a symptom of the non-arthritic autoimmune disorder without a systemic toxicity resulting.

13. The method of claim 12, wherein the Clostridial neurotoxin and cytokine inhibitor are administered in amounts that provide a greater relief of the at least one symptom of the non-arthritic autoimmune disorder compared to the administration of only the Clostridial neurotoxin or the cytokine inhibitor alone to a patient to treat the same non-arthritic autoimmune disorder.

14. The method of claim 12, wherein the Clostridial neurotoxin is selected from the group consisting of botulinum toxins types A, B, $C_1$, D, E, F, and G.

15. The method of claim 12, wherein the Clostridial neurotoxin is botulinum toxin type A.

16. The method of claim 12, wherein the botulinum toxin administered is a botulinum toxin type A in an amount from no less than about 1 unit and no more than about 50 units of a botulinum toxin type A per injection site per patient treatment session.

17. The method of claim 12, wherein the botulinum toxin administered is botulinum toxin type A in an amount from no less than about 2 unit and no more than about 200 units of a botulinum toxin type A per injection site per patient treatment session.

18. The method of claim 12, wherein the botulinum toxin administered is a botulinum toxin type B in an amount from no less than about 40 unit and no more than about 2500 units of a botulinum toxin type B per injection site per patient treatment session.

19. The method of claim 12, wherein the Clostridial neurotoxin and the cytokine inhibitor are administered to the patient in a single composition.

20. The method of claim 12, wherein the Clostridial neurotoxin is administered to the thymus gland of the patient.

21. The method of claim 12, wherein the Clostridial neurotoxin is botulinum toxin type A and the cytokine inhibitor is selected from the group consisting of cytokine neutralizers, cytokine receptor blockers, anti-inflammatory cytokines, and combinations thereof.

22. The method of claim 12, wherein the Clostridial neurotoxin is administered in an amount effective in inhibiting neuropeptide mediated inflammation, and the cytokine inhibitor is administered in an amount effective in inhibiting cytokine mediated inflammation.

23. The method of claim 1, wherein the non-arthritic autoimmune disorder is a systemic non-arthritic autoimmune disease.

24. The method of claim 1, wherein the non-arthritic autoimmune disorder is a localized non-arthritic autoimmune disease.

25. The method of claim 12, wherein the non-arthritic autoimmune disorder is selected from the group consisting of scleroderma or CREST syndrome, Sjogren's syndrome, Goodpasture's syndrome, Wegener's granulomatosis, temporal arteritis/giant cell arteritis, Type 1 Diabetes Mellitus, Hashimoto's thyroiditis, Graves' disease, celiac disease, Crohn's diseases, ulcerative colitis, multiple sclerosis, Guillain-Barre syndrome, Addison's disease, primary biliary sclerosis, sclerosing cholangitis, autoimmune hepatitis, Raynaud's phenomenon, pernicious anemia, Addison's disease, dermatomyositis, myasthenia gravis, Pemphigus vulgaris, autoimmune hemolytic anemia, autoimmune thrombocytopenic purpura, vasculitis, and amyotrophic lateral schlerosis.

26. The method of claim 12, wherein the non-arthritic autoimmune disorder is a systemic non-arthritic autoimmune disease.

27. The method of claim 12, wherein the non-arthritic autoimmune disorder is a localized non-arthritic autoimmune disease.

* * * * *

UNITED STATES PATENT AND TRADEMARK OFFICE
CERTIFICATE OF CORRECTION

| | | |
|---|---|---|
| PATENT NO. | : 8,105,611 B2 | |
| APPLICATION NO. | : 11/156502 | |
| DATED | : January 31, 2012 | |
| INVENTOR(S) | : Pamela D. Van Schaack | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 645 days.

On Title page, item (56), under "OTHER PUBLICATIONS", in column 2, line 19, delete "Otolatyngol" and insert -- Otolaryngol --, therefor.

On Title page, item (56), under "OTHER PUBLICATIONS", in column 2, line 28, delete "Synaptoxomes" and insert -- Synaptosomes --, therefor.

On Title page, item (56), under "OTHER PUBLICATIONS", in column 2, line 29, delete "Nauny-Schmiedeberg's" and insert -- Naunyn-Schmiedeberg's --, therefor.

On Title page 2, item (56) under "OTHER PUBLICATIONS", in column 1, line 7, delete "Nauny-Schmiedeberg's" and insert -- Naunyn-Schmiedeberg's --, therefor.

On Title page 2, item (56) under "OTHER PUBLICATIONS", in column 1, line 34, delete "asthama"," and insert -- asthma", --, therefor.

On Title page 2, item (56) under "OTHER PUBLICATIONS", in column 2, line 11, delete "hyperhydrosis" and insert -- hyperhidrosis --, therefor.

On Title page 2, under "OTHER PUBLICATIONS", in column 2, line 30, delete "Cytokenes" and insert -- Cytokines --, therefor.

In column 2, line 59, delete "schlerosis" and insert -- sclerosis --, therefor.

In column 3, line 41, delete "rituxamab," and insert -- rituximab, --, therefor.

In column 6, line 6, delete "hemaglutinin" and insert -- hemagglutinin --, therefor.

Signed and Sealed this
Fifth Day of June, 2012

David J. Kappos
*Director of the United States Patent and Trademark Office*

CERTIFICATE OF CORRECTION (continued)
U.S. Pat. No. 8,105,611 B2

In column 6, line 7, delete "nonhemaglutinin" and insert -- nonhemagglutinin --, therefor.

In column 8, line 33, delete "supercihii" and insert -- supercilii --, therefor.

In column 8, line 49, delete "sublimus:" and insert -- sublimis: --, therefor.

In column 9, line 5, delete "hyperhydrosis." and insert -- hyperhidrosis. --, therefor.

In column 9, line 7, delete "Lalyngoscope" and insert -- Laryngoscope --, therefor.

In column 9, line 21, delete "Nauny-Schmiedeberg's" and insert -- Naunyn-Schmiedeberg's --, therefor.

In column 9, line 22, delete "Nauny-Schmiedeberg's" and insert -- Naunyn-Schmiedeberg's --, therefor.

In column 10, line 22, delete "gangliocide" and insert -- ganglioside --, therefor.

In column 10, line 59, delete "norepinephine." and insert -- norepinephrine. --, therefor.

In column 11, line 59, delete "implant" and insert -- implant. --, therefor.

In column 18, line 39, delete "schlerosis" and insert -- sclerosis --, therefor.

In column 24, line 44, in claim 11, delete "schierosis." and insert -- sclerosis. --, therefor.

In column 25, line 7, in claim 17, delete "is" and insert -- is a --, therefor.

In column 26, line 22, in claim 25, delete "schlerosis." and insert -- sclerosis. --, therefor.